US006986276B2

(12) United States Patent
Gysling et al.

(10) Patent No.: US 6,986,276 B2
(45) Date of Patent: Jan. 17, 2006

(54) DEPLOYABLE MANDREL FOR DOWNHOLE MEASUREMENTS (75) Inventors: Daniel L. Gysling, Glastonbury, CT (US); Stuart E. Ferguson, Houston, TX (US)

(73) Assignee: Weatherford/Lamb, Inc., Houston, TX (US)

( * ) Notice: Subject to any disclaimer, the term of this patent is extended or adjusted under 35 U.S.C. 154(b) by 135 days.

(21) Appl. No.: 10/384,269

(22) Filed: Mar. 7, 2003

(65) Prior Publication Data
US 2004/0173010 A1    Sep. 9, 2004

(51) Int. Cl.
G01N 9/00    (2006.01)
(52) U.S. Cl. ............... 73/32 A; 73/61.79; 73/64.44
(58) Field of Classification Search ............ 73/32 A, 73/24.05, 61.79, 61.41, 61.44, 61.47, 61.49, 73/64.44
See application file for complete search history.

(56) References Cited

U.S. PATENT DOCUMENTS

| | | | |
|---|---|---|---|
| 3,149,492 A | 9/1964 | Weinberg | |
| 3,851,521 A | 12/1974 | Ottenstein | |
| 4,080,837 A | 3/1978 | Alexander et al. | 73/61.45 |
| 4,114,439 A | 9/1978 | Fick | 73/861.28 |
| 4,144,768 A | 3/1979 | Andersson | |
| 4,159,646 A | 7/1979 | Paulsen | |
| 4,164,865 A | 8/1979 | Hall | |
| 4,236,406 A | 12/1980 | Reed | |
| 4,275,602 A | 6/1981 | Fujishiro | |
| 4,445,389 A | 5/1984 | Potzick | |
| 4,499,418 A | 2/1985 | Helms | |
| 4,515,473 A | 5/1985 | Mermelstein | |
| 4,520,320 A | 5/1985 | Potzick | |
| 4,546,649 A | 10/1985 | Kantor | 73/168 |
| 4,706,501 A | 11/1987 | Atkinson | |
| 4,788,852 A | 12/1988 | Martin | |
| 4,813,270 A | 3/1989 | Baillie | |
| 4,862,750 A | 9/1989 | Nice | |

(Continued)

FOREIGN PATENT DOCUMENTS

EP    0684458    5/1995

(Continued)

OTHER PUBLICATIONS

U.S. Appl. No. 10/010,183, filed Nov. 7, 2001, Gysling.

(Continued)

Primary Examiner—Thomas P. Noland
Assistant Examiner—John C Hanley
(74) Attorney, Agent, or Firm—Patterson & Sheridan, L.L.P.

(57) ABSTRACT

The disclosed apparatus comprises a phase fraction meter and a compliant mandrel deployable within a production pipe, and may further comprise a flow velocity meter. The mandrel allows the determination of the phase fraction for a fluid comprising three phases by providing an additional cross sectional compliance within the conduit, thereby allowing the density of the fluid to be determined. The mandrel also provides a specified blockage through the flow velocity meter, thereby increasing flow velocity through the meter. This allows flow rate measurements in conditions under which flow velocity in the under-restricted cross-sectional area of the pipe would normally be very low. Further, the mandrel can provide a specified restriction in the pipe, i.e., a venturi. By measuring the differential pressure across the venturi and utilizing the measured fluid velocity from the flow velocity meter, the density of the fluid mixture can be calculated. This calculated density can be used in conjunction with other measurements to determine phase fractions or to double check or to calibrate the phase fraction meter. The mandrel can be deployed without removing the meter from the conduit, allowing for easy adaptation to changing flow parameters and fluid compositions.

54 Claims, 3 Drawing Sheets

U.S. PATENT DOCUMENTS

| | | |
|---|---|---|
| 4,864,868 A | 9/1989 | Khalifa .................... 73/861.24 |
| 4,884,457 A | 12/1989 | Hatton |
| 4,896,540 A | 1/1990 | Shakkottai |
| 4,932,262 A | 6/1990 | Wlodarczyk |
| 4,947,127 A | 8/1990 | Helms |
| 4,950,883 A | 8/1990 | Glenn .................... 250/227.14 |
| 4,976,151 A | 12/1990 | Morishita |
| 4,996,419 A | 2/1991 | Morey .................... 250/227.18 |
| 5,024,099 A | 6/1991 | Lee |
| 5,031,460 A | 7/1991 | Kanenobu |
| 5,040,415 A | 8/1991 | Barkhoudarian |
| 5,051,922 A | 9/1991 | Toral |
| 5,058,437 A | 10/1991 | Chaumont |
| 5,083,452 A | 1/1992 | Hope .................... 73/61 R |
| 5,099,697 A | 3/1992 | Agar |
| 5,115,670 A | 5/1992 | Shen .................... 73/61.41 |
| 5,152,181 A | 10/1992 | Lew |
| 5,207,107 A | 5/1993 | Wolf |
| 5,218,197 A | 6/1993 | Carroll .................... 250/227.16 |
| 5,317,576 A | 5/1994 | Leonberger et al. ........... 372/6 |
| 5,321,991 A | 6/1994 | Kalotay |
| 5,347,873 A | 9/1994 | Vander Heyden |
| 5,361,130 A | 11/1994 | Kersey |
| 5,363,342 A | 11/1994 | Layton et al. ............... 367/149 |
| 5,367,911 A | 11/1994 | Jewell et al. ............ 73/861.08 |
| 5,372,046 A | 12/1994 | Kleven |
| 5,398,542 A | 3/1995 | Vasbinder .................... 73/40.5 |
| 5,401,956 A | 3/1995 | Dunphy et al. ........ 250/227.18 |
| 5,426,297 A | 6/1995 | Dunphy et al. ........ 250/227.23 |
| 5,440,932 A | 8/1995 | Wareham |
| 5,493,390 A | 2/1996 | Varasi et al. .................... 356/32 |
| 5,493,512 A | 2/1996 | Peube et al. ................. 364/510 |
| 5,513,913 A | 5/1996 | Ball et al. .................... 374/120 |
| 5,564,832 A | 10/1996 | Ball et al. .................... 374/161 |
| 5,576,497 A | 11/1996 | Vignos |
| 5,591,922 A | 1/1997 | Segeral et al. ........... 73/861.04 |
| 5,597,961 A | 1/1997 | Marrelli |
| 5,639,667 A | 6/1997 | Heslot |
| 5,642,098 A | 6/1997 | Santa Maria |
| 5,644,093 A | 7/1997 | Wright |
| 5,654,551 A | 8/1997 | Watt |
| 5,670,720 A | 9/1997 | Clark |
| 5,680,489 A | 10/1997 | Kersey |
| 5,689,540 A | 11/1997 | Stephenson |
| 5,708,211 A | 1/1998 | Jepson et al. ............ 73/861.04 |
| 5,730,219 A | 3/1998 | Tubel |
| 5,732,776 A | 3/1998 | Tubel |
| 5,741,980 A | 4/1998 | Hill et al. ................. 73/861.04 |
| 5,803,167 A | 9/1998 | Bussear |
| 5,804,713 A | 9/1998 | Kluth |
| 5,842,347 A | 12/1998 | Kinder |
| 5,845,033 A | 12/1998 | Berthold et al. ............... 385/12 |
| 5,906,238 A | 5/1999 | Carmody |
| 5,907,104 A | 5/1999 | Cage |
| 5,908,990 A | 6/1999 | Cummings |
| 5,925,821 A | 7/1999 | Bousquet |
| 5,925,879 A | 7/1999 | Hay |
| 5,939,643 A | 8/1999 | Oertel |
| 5,956,132 A | 9/1999 | Donzier |
| 5,959,547 A | 9/1999 | Tubel |
| 5,963,880 A | 10/1999 | Smith |
| 5,975,204 A | 11/1999 | Tubel |
| 5,992,519 A | 11/1999 | Ramakrishnan |
| 5,996,690 A | 12/1999 | Shaw |
| 6,002,985 A | 12/1999 | Stephenson |
| 6,003,383 A | 12/1999 | Zielinska |
| 6,003,385 A | 12/1999 | De Vanssay |
| 6,009,216 A | 12/1999 | Pruett |
| 6,016,702 A | 1/2000 | Maron |
| 6,158,288 A | 12/2000 | Smith .................... 73/861.25 |
| 6,216,532 B1 | 4/2001 | Stephenson |
| 6,233,374 B1 | 5/2001 | Ogle |
| 6,279,660 B1 | 8/2001 | Hay |
| 6,354,147 B1 | 3/2002 | Gysling |
| 6,782,150 B2 * | 8/2004 | Davis et al. .................. 385/12 |
| 2002/0064331 A1 | 5/2002 | Davis et al. |
| 2002/0134144 A1 | 9/2002 | Gysling et al. |
| 2003/0084707 A1 * | 5/2003 | Gysling .................... 73/32 A |
| 2003/0089161 A1 * | 5/2003 | Gysling .................... 73/32 A |
| 2003/0136186 A1 * | 7/2003 | Gysling .................... 73/64.53 |

FOREIGN PATENT DOCUMENTS

| | | |
|---|---|---|
| FR | 2 357 868 | 7/1976 |
| JP | 406082281 | 9/1992 |
| WO | WO 93/14382 | 7/1993 |
| WO | WO 96/04528 | 2/1996 |
| WO | WO 00/00793 | 1/2000 |
| WO | WO 2004/003484 | 1/2004 |
| WO | WO 2004/015377 | 2/2004 |

OTHER PUBLICATIONS

U.S. Appl. No. 10/186,382, filed Jun. 28, 2002, Gysling.

U.S. Appl. No. 10/342,052, filed Jan. 14, 2003, Gysling.

Mesch, F. (1990) "Speed and Flow Measurement by an Intelligent Correlation System", Advances in Instrumentation and Control, Research Triangle Park, NC, part 4, p. 1899-1914.

Gysling, D. (1999) "Development of a Fiber Optic Downhole Multiphase Flow Meter", in "Field Applications & New Technologies for Multiphase Metering", Multiphase Technology Series Conference, Aberdeen, Scotland.

Beranek, L. and Ver, I. (1992) in "Noise and Vibration Control Engineering, Principles and Application", John Wiley & Sons, Inc., Chapter 14, p:537-541.

Dowling, A. and Williams, J. in "Sound and Sources of Sound", Ellis Horwood Limited, Section 4, p:79-80.

Kersey, A. et al. (1993) "Multiplexed Fiber Bragg Grating Strain-Sensor System with a Fiber Fabry-Perot Wavelength Filter", Optics Letters, 18:1370-1372.

Dandridge, A. & Cogdell, G. (1991) "Fiber Optic Sensors for Navy Applications", IEEE, LCS, 2:81-89.

Nielsen, R. (1991) "Sonar Signal Processing", Artech Huse Inc., Chapter 2, p:51-59.

Krim A. and Viberg M. (1996) "Two Decades of Array Signal Processing Research", IEEE Signal Processing Magazine, p:67-94.

Kersey A. and Darkin, J., Editors (1992) SPIE vol. 1586, "Distributed and Multiplexed Fiber Optic Sensors", p:1-243.

Nerby et al. "A cost effective technique for production well testing", (1995) Offshore Technology Conference, p:505-515.

U.K. Search Report, Application No. GB0405069.6, dated Jul. 8, 2004.

* cited by examiner

DEPLOYABLE MANDREL FOR DOWNHOLE MEASUREMENTS

CROSS REFERENCE TO RELATED APPLICATIONS

This application contains subject matter related to U.S. patent application Ser. No. 10/010,183, filed Nov. 7, 2001, which is incorporated herein by reference in its entirety.

TECHNICAL FIELD

This invention relates to measuring fluid parameters in pipes, and more particularly to measuring fluid composition, volumetric flow, or other fluid parameters using at least one flow meter assisted by a deployable mandrel.

BACKGROUND OF THE INVENTION

In many industries it is desirable to measure various parameters of fluids or fluid mixtures in pipes, including the temperature, pressure, composition (i.e., phase fraction, e.g., 10% water, 90% oil), flow rate, density, and/or the speed of sound (SOS) in the is fluid. (As used herein, "fluid" may refer to a liquid or gas, and a "fluid mixture" may be mixtures of liquids or gases or solids). Different sensor arrangements, referred to generically as "flow meters," can be used to measure these parameters, such as those that are disclosed in the following U.S. patent applications, which are incorporated herein by reference in their entireties, and which may have issued as U.S. patents: Ser. No. 09/740,760, filed Nov. 29, 2000; Ser. No. 09/344,070, filed Jun. 25, 1999; Ser. No. 09/346,607, filed Jul. 2, 1999; Ser. No. 09/344,093, filed Jun. 25, 1999; Ser. No. 09/345,827, filed Jul. 2, 1999; Ser. No. 09/519,785, filed Mar. 7 2000; Ser. No. 09/346,606, filed Jul. 2, 1999; Ser. No. 09/346,604, filed Jul. 2, 1999; Ser. No. 09/346,605, filed Jul. 2, 1999; Ser. No. 09/344,094, filed Jun. 25, 1999; Ser. No. 10/010,183, filed Nov. 7, 2001; Ser. No. 09/344,069, filed Jun. 25, 1999; and Ser. No. 10/186,382, filed Jun. 28, 2002.

A flow meter typically comprises a sensor, a sensor array, or multiple sensor arrays. In many of these flow meters, the sensors may comprise fiber optic sensors, possibly incorporating fiber Bragg gratings (FBGs), which can be mounted or coiled around the pipe containing the fluid to be measured. Other flow meters allow optical devices or other sensing devices to be ported or placed within the pipe to make the required measurements. When one uses a fiber optic based flow meter, the fluid or fluid mixture parameters may be measured without the need to "tap in" to the pipe, as many of these parameters may be sensed externally to the pipe though the means disclosed in the above incorporated references. Often, these externally mounted sensors are "passive" sensors in the sense that they do not require stimulating the fluid or fluid mixture of interest by external means, but instead make the required measurements simply by sensing various naturally occurring fluid perturbations.

In the oil and gas industry, or comparable industries, it is desirable to measure, in situ, the flow produced from an oil well. Typically the produced fluid mixture may be comprised of three components or phases, such as oil, water, and gas, which may additionally contain other components, such as solids (e.g., rocks or sand) or other liquid phases. In a production environment, it is often useful to determine the phase fraction, or composition, of the fluid mixture being measured, as well as the speed of the flowing fluid or fluid mixture.

Techniques for measuring a fluid or fluid mixture flow rate exist in the prior art. For example, in U.S. patent application Ser. No. 09/346,607, entitled "Flow Rate Measurement Using Unsteady Pressures," filed Jul. 2, 1999, incorporated herein by reference in its entirety, there is disclosed a flow rate meter which preferably utilizes fiber optic sensors. At least two fiber optic sensors are disposed at two different axial locations along a pipe containing the fluid to be measured. The first and second sensors are spaced at a predetermined axial distance apart. Naturally occurring pressure disturbances in the fluid, such as acoustic pressure waves and vortical pressure waves, perturb the first sensor through the wall of the pipe, creating a first time-based pressure signal. When the pressure disturbance, or pressure field, moves from the first sensor to the second sensor, a second time-based pressure signal is measured. The first and second signals can then be cross-correlated using well-known techniques to determine the time delay between the pressure signals. Dividing the known axial distance by this time delay provides the velocity of the fluid flowing through the pipe. The velocity may then be converted to volumetric flow rate by multiplying the velocity by the cross-sectional area of the pipe. Optionally, the sensors may comprise filters capable of filtering out pressure disturbances caused by acoustic pressure waves and other long wavelength pressure disturbances. This filtering results in a pressure signal largely indicative of vortical pressure disturbances occurring naturally in the fluid, thereby reflecting a more accurate depiction of the fluid velocity and flow rate.

Other flow rate techniques using venturis are also known in the art. For example, U.S. Pat. No. 5,591,922, entitled "Method and Apparatus for Measuring Multiphase Flow," issued Jan. 7, 1997, and which is incorporated by reference herein in its entirety, describes a meter having a pair of venturis within a pipe spaced from one another at an axial distance. As is well known, the venturi causes a pressure difference ($\Delta P$) at each venturi, which are measured. These differential pressure signals are cross-correlated to determine a time delay. Dividing the axial distance between the venturis by the time delay results in the flow velocity. Furthermore, given the volume between the two differential pressure measurements, the time delay makes it possible to determine the total volume flow rate by dividing the volume by the time delay.

Flow meters for determining phase fraction ("phase fraction meter") in a fluid mixture are also known in the art. For example in U.S. Pat. No. 6,354,147, entitled "Fluid Parameter Measurement in Pipes Using Acoustic Pressures," issued Mar. 12, 2002, which is incorporated by reference herein in its entirety, a spatial array of pressure sensors, preferably fiber optic sensors, are coupled to the outside of the pipe. Each sensor measures acoustic pressure disturbances and then provides acoustic pressure signals that are then used to determine the speed of sound of the mixture. Because the speed of sound of a given mixture is related to the fluid composition, the measured speed of sound can be used to directly determine the phase fraction of at least two-phase mixture, although it may be necessary or helpful to combine the measured sound speed with other known quantities to determine the phase fraction of a fluid containing more than two phases.

Often these various types of flow meters will be used in conjunction with each other to measure various fluid parameters of the device. For example, a flow rate meter may be used on one section of the pipe, followed downstream by a phase fraction meter, or vice versa. Or, these flow meters may be combined into an integrated flow meter apparatus, as described in patent application Ser. No. 09/740,760, entitled "Apparatus for Sensing Fluid in a Pipe," filed Nov. 29, 2000, incorporated herein by reference in its entirety.

While these prior art techniques generally perform well, they may not be optimized for measuring the parameters of fluid mixtures having more than two phases, such as occurs following "gas breakthrough" during oil production. During early production, reservoir pressure is often sufficient for the produced hydrocarbons to remain under-saturated with gas as the fluids enter the production tubing. In this condition, a flow meter located at or near the sand face would encounter liquids only because the gases remain dissolved in the liquids. As the fluids move higher up the production string, the pressure decreases to below the "bubble point" of the fluids, allowing free gas to break out of the produced fluids. As the reservoir pressure is depleted, the point at which gas comes out of solution moves down the production tubing and often eventually into the reservoir itself. Consequently, any production flow meter would encounter free gas. The presence of gas can degrade the ability of a meter to measure fluid parameters, even if the meter was performing adequately up to the point of gas breakthrough.

The art would therefore benefit from ways to improve the performance of these and other traditional flow meters, especially with regard to their ability to measure more than two phases. Additionally, it would be desirable that the flow meter can adapt to changing conditions within the pipe, for example, as the breakthrough point moves down the well as a result of reservoir depletion.

SUMMARY OF THE INVENTION

The disclosed apparatus comprises a phase fraction meter and a compliant mandrel deployable within a production pipe, and may further comprise a flow velocity meter. The mandrel allows the determination of the phase fraction for a fluid comprising three phases by providing an additional cross sectional compliance within the conduit, thereby allowing the density of the fluid to be determined. The mandrel also provides a specified blockage through the flow velocity meter, thereby increasing flow velocity through the meter. This allows flow rate measurements in conditions under which flow velocity in the under-restricted cross-sectional area of the pipe would normally be very low. Further, the mandrel can provide a specified restriction in the pipe, i.e., a venturi. By measuring the differential pressure across the venturi and utilizing the measured fluid velocity from the flow velocity meter, the density of the fluid mixture can be calculated. This calculated density can be used in conjunction with other measurements to determine phase fractions or to double check or to calibrate the phase fraction meter. The mandrel can be deployed without removing the meter from the conduit, allowing for easy adaptation to changing flow parameters and fluid compositions.

BRIEF DESCRIPTION OF THE DRAWINGS

The features and advantages of the invention will be apparent from consideration of the subsequent detailed description and the accompanying drawings.

DESCRIPTION OF ILLUSTRATIVE EMBODIMENTS

In the disclosure that follows, in the interest of clarity, not all features of actual commercial implementations of a deployable compliant mandrel for downhole multiphase flow measurement and related techniques are described. It will of course be appreciated that in the development of any such actual implementation, as in any such project, numerous engineering and design decisions must be made to achieve the developers' specific goals, e.g., compliance with mechanical and business related constraints, which will vary from one implementation to another. While attention must necessarily be paid to proper engineering and design practices for the environment in question, it should be appreciated that development of a deployable compliant mandrel for downhole multiphase flow measurement and related techniques would nevertheless be a routine undertaking for those of skill in the art given the details provided by this disclosure, even if such development efforts are complex and time-consuming.

Figure 1A:
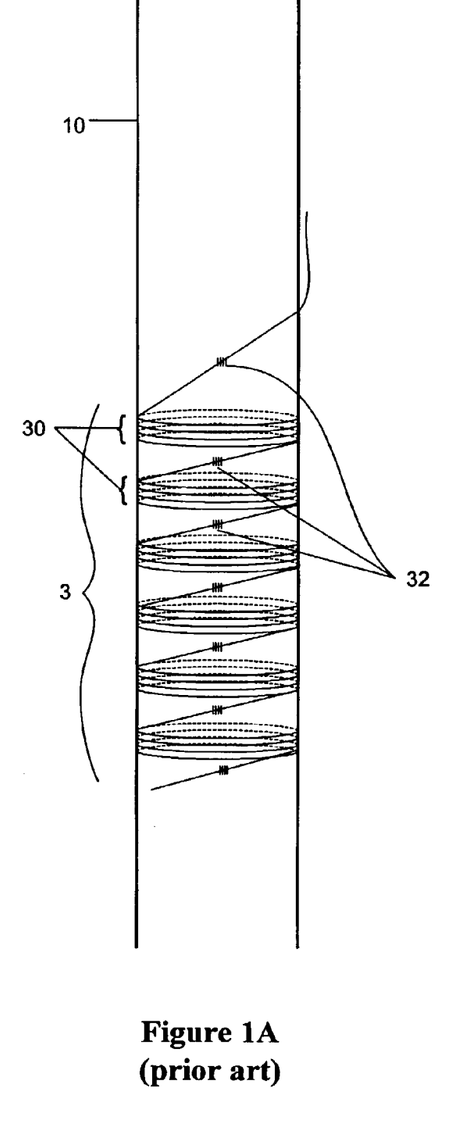
FIG. 1a is a diagram of a prior art phase fraction meter attached to a production pipe.

FIG. 1a shows a prior art phase fraction meter 3 attached to the outside of a production pipe 10, or a specialized pipe section coupled to the production pipe, which is preferably deployed down a well bore. The phase fraction meter 3 can constitute the meter disclosed in U.S. Pat. No. 6,354,147, entitled "Fluid Parameter Measurement in Pipes Using Acoustic Pressures," issued Mar. 12, 2002, which is incorporated by reference herein in its entirety. The details of this phase fraction meter are not disclosed herein, but preferably includes passive fiber optic based sensors 30 employing or working in conjunction with fiber Bragg gratings (FBGs) 32. The sensors 30 preferably comprise wraps of fiber optic cable wound around and in contact with the outside surface of the production pipe 10. The sensors are sensitive to pressures present within the pipe 10, and will accordingly change in length in response to such pressures. The sensors 30 are bounded by fiber Bragg gratings 32, which allows the changes in length of the sensors 30 (and hence the pressure inside of the pipe) to be assessed by interferometric or time-of-flight techniques, as is disclosed in U.S. patent application Ser. No. 09/726,059, filed Nov. 29, 2002, which is incorporated herein by reference. So arranged, the sensors 30 in meter 3 are coupled in a time division multiplexing approach, although wavelength division multiplexing could also be used as one skilled in the art will appreciate. As disclosed in the incorporated references, it is preferable to house the phase fraction meter 3 in a housing formed around and in contact with the production pipe 10, which is not shown for clarity. The sensor housing may be evacuated.

With reference to U.S. Pat. No. 6,354,147, one of skill in the art will appreciate that the speed of sound in a fluid is related to the phase fractions of the fluid and the densities of the components of the fluid by the following equations:

$$\frac{1}{\rho_{mix}a_{mix}^2} = \sum_{i=1}^{N}\frac{\phi_i}{\rho_i a_i^2}; \rho_{mix} = \sum_{i=1}^{N}\phi_i\rho_i; \text{ and } \sum_{i=1}^{N}\phi_i = 1 \quad (1)$$

where $\rho_{mix}$ is the density of the fluid, $\rho_i$ is the density of the $i^{th}$ component, $a_{mix}$ is the speed of sound in the fluid, $a_i$ is the speed of sound in the $i^{th}$ component, $\phi_i$ is the phase fraction of the $i^{th}$ component, and N is the number of components or phases in the fluid (e.g., oil, gas, and water). The density ($\rho_i$) and speed of sound ($a_i$) for each of the individual components can be known or measured independently. The phase fraction meter measures the speed of sound ($a_{mix}$) in the fluid.

For a fluid consisting of two components, the equations above yield a system of three equations and three unknowns, the unknowns being $\rho_{mix}$, $\phi_1$, and $\phi_2$. The equations are therefore easily solvable for the phase fractions of each of the components. However, if there are more than two components in the fluid, there will be more unknowns than equations, and therefore more information will be required to uniquely solve for the phase fractions, $\phi_i$. Specifically, for a three-phase mixture, one would wish to know the density of the mixture, $\rho_{mix}$, to yield a system of three equations and three unknowns, $\phi_1$, $\phi_2$, and $\phi_3$, which could be discretely solved for.

One embodiment of the present invention solves this problem by taking advantage of the inherent fact that the propagation of sound waves through a fluid in a pipe is influenced by the structural properties of the pipe. For example, the measured speed of sound is influenced by the compliance of the pipe. If the pipe is surrounded with a media of negligible acoustic impedance, the speed of sound of the fluid within the pipe is related to the compliance of the pipe $\sigma$ by:

$$\frac{1}{\rho_{mix}a_{measured}^2} = \frac{1}{\rho_{mix}a_{mix}^2} + \sigma, \text{ where } \sigma = \frac{2R}{Et} \quad (2)$$

and where R is the pipe radius, t is the pipe wall thickness, E is the Young's modulus for the pipe material, and $a_{measured}$ is the measured speed of sound for the fluid yielded by the phase fraction (i.e. speed of sound) meter 3. As described in U.S. Pat. No. 6,354,147, equation (2) is important because it relates the speed of sound as measured by the phase fraction meter ($a_{measured}$) to the actual speed of sound ($a_{mix}$) that is needed in equation (1).

The effect of the compliance on the measured speed of sound is not only important for relating the measured speed of sound to the actual speed of sound, but also can provide an additional variable that can be exploited to determine the density of the fluid, $\rho_{mix}$. The change in the speed of sound in pipes having different cross sectional compliances is:

$$a_{measured,1} - a_{measured,2} = \frac{1}{\sqrt{\frac{1}{a_{mix}^2} + \rho_{mix}\sigma_1}} - \frac{1}{\sqrt{\frac{1}{a_{mix}^2} + \rho_{mix}\sigma_2}} \quad (3)$$

Thus, if a pipe containing the fluid to be measured has two sections of different compliancies, $\sigma_1$ and $\sigma_2$, the speed of sound, $a_{measured,1}$ and $a_{measured,2}$ can be measured at those two locations using two different phase fraction meters. Using these measurements, the density of the fluid can be determined by the following equation:

$$\rho_{mix} = \frac{1}{(\alpha-1)\sigma_2}\left(\frac{1}{a_{measured,1}^2} - \frac{1}{a_{measured,2}^2}\right) \quad (4)$$

where $\sigma_2$ is the compliance of the more rigid section and $\alpha$ is the ratio of the compliances (i.e., $\sigma_1$ divided by $\sigma_2$). Adding $\rho_{mix}$ to equations (1) above yields a set of three equations and therefore provides a means of determining the phase fractions of a three component mixture by measuring the speed of sound of the mixture in conduits having different cross sectional compliances. Further details concerning this technique are disclosed in U.S. patent application Ser. No. 10/010,183, filed Nov. 7, 2001, which is incorporated herein by reference.

Figure 1B:
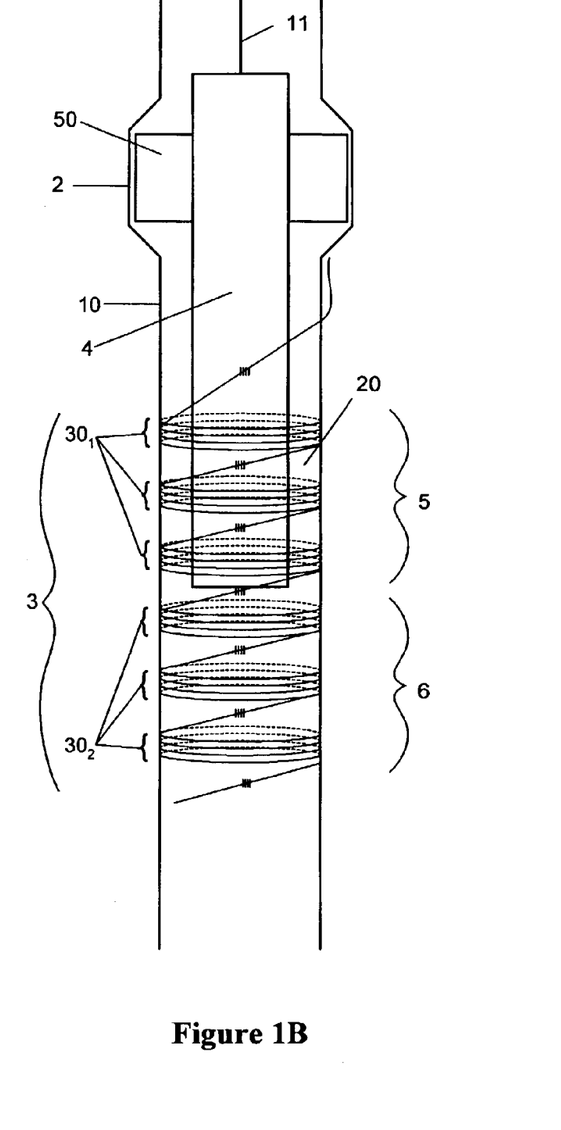
FIG. 1b is a diagram of a deployable mandrel shown deployed in a production pipe.

For many applications, substituting piping of different materials or compliancies, as disclosed in the above-mentioned patent application, may be a difficult or impractical method of obtaining speed of sound measurements and/or phase fraction determinations. Thus, an alternative embodiment to solve for fluid density, $\rho_{mix}$, and hence phase fraction, is to use a compliant mandrel, as shown in FIG. 1b. As shown in FIG. 1b, a production pipe 10 has a mandrel 4 deployed therein by a wireline 11. Wirelines to deploy and/or retrieve down hole tools are well known, and are the preferred method of deploying the mandrel 4, but deployment may be achieved by other well-known means as well, such as by use of coiled tubing or other known well intervention techniques. A turning tool (not shown) connects the mandrel 4 to the wireline 11.

As shown, the cylindrical mandrel 4 is brought into proximity to phase fraction meter 3 by seating the mandrel 4 in position using a seating nipple 2 formed in the production pipe 10. The seating nipple 2 is formed in the production tube 10 in proximity to the phase fraction meter 3 (also formed on the production pipe 10) such that the mandrel 4 when seated will appropriately penetrate some distance through the phase fraction meter 3 as will be explained shortly. To allow for proper seating at the seating nipple 2, the mandrel 4 includes appropriate deployable or hinged keys or "dogs" 50 which interface with the seating nipple 2 to hold the mandrel in place during production. Many examples of seating nipples 2 and interfacing dogs 50 are well known in the art, and accordingly, description of these features are idealized for simplicity in the drawings. For further reference, the Sur-Set™ flow control system manufactured by Baker Oil Tools discloses a nipple/dog configuration usable in the context of the present disclosure. As the mandrel 4 operates by virtue of fluid in the pipe 10 flowing around it, it is preferred that the dogs 50 do not substantially impede the flow of produced fluids in the annulus between the mandrel and the seating nipple 2.

In operation, the mandrel 4 is deployed into the production pipe 10 using the wireline 11, preferably when production is temporarily halted. After the mandrel is seated at the nipple 2, the running tool releases from the mandrel 4 and is retrieved from the production pipe 10 along with the wireline, leaving the mandrel seated in place. Production of fluids can then be restarted, and fluid dynamic measurements taken as discussed further below. At some point later, the mandrel 4 can be retrieved if necessary from the production pipe 10 by deploying a pulling tool via a wireline.

As is well known, the pulling tool latches onto the mandrel 4, unlocks the mandrel from the seating nipple 2, thus allowing the mandrel 4 to be retrieved form the well. As these mandrel deployment and retrieval procedures are well known, they are not further discussed.

The mandrel 4 interacts with the speed of sound or phase fraction meter 3 and, in the embodiment of FIG. 1b, appears partially within the zone of the production pipe spanned by the meter 3. Thus, zone 5 of the measurement region of the meter contains a portion of the mandrel 4, and zone 6 does not contain any portion of the mandrel. The area between the mandrel 4 and the pipe 10 in zone 5 constitutes a fluid annulus 20 around which the produced fluid flows.

The material used to construct the mandrel 4 is not particularly important, but should be formed of a material suitable for the downhole environment that it will encounter, such as stainless steel. The mandrel is preferably hollow to provide it suitable compliancy in comparison to the compliancy of the production pipe 10 around which the meter 3 is affixed. The specific dimensions and thickness of the mandrel 4 can vary greatly depending upon the environment in which it will be used, and will involve considerations of the expected hydrostatic pressures encountered, the inside diameter of the production pipe, the length of the meter 3, etc. Generally, the outside diameter of the mandrel 4 will be smaller than the inside diameter of the production pipe, but not large enough to significantly impede the production of fluids through the production pipe 10. Determination of the optimal physical parameters for the mandrel 4 may also require some degree of experimentation. However, the following description of the physics and fluid dynamics involved will assist one skilled in the art to design an appropriate mandrel for a given application.

If one assumes that the pipe 10 has a radius $R_1$, a thickness $t_1$, and a modulus $E_1$, and that the mandrel 4 has a radius $R_2$, a thickness $t_2$, and a modulus $E_2$, then the cross sectional compliance in the annulus 20 can be expressed as:

$$\sigma = \frac{2\left(\frac{R_2^2}{E_2 t_2} + \frac{R_1^2}{E_1 t_1}\right)}{R_2^2 - R_1^2} \quad (5)$$

assuming that both the outside of the pipe (i.e., the sensor housing) and the inside of the mandrel are evacuated or are negligible given the environment in question.

In a preferred embodiment, the speed of sound is simultaneously measured in zones 5 and 6 to enable the calculation of the fluid mixture density, and hence the phase fraction of a three phase liquid in accordance with the system of equations set forth above. By having the mandrel 4 deployed through a known portion of the phase fraction meter 3, those sensors wraps $30_1$ within the meter can be queried and processed to determine the speed of sound in the zone 5 (i.e., $a_{measured,1}$) in accordance with equation (2) above, where the compliance of the pipe system, $\sigma_1$, is determined in accordance with equation (5) above. The remaining sensor wraps $30_2$ can be queried and processed to determine the speed of sound in zone 6 (i.e., $a_{measured,2}$), where the compliance of the pipe, $\sigma_2$, is determined in accordance with equation (2) above. Because the sensors $30_1$ and $30_2$ are time division multiplexed, resolution of the sensors appearing in each zone 5 or 6 are easy to distinguish. From these two speed of sound measurements, and from computing the two compliances, the density of the fluid, $\rho_{mix}$, can be calculated in accordance with equation (4) above, which allows for the phase fractions of a three phase fluid to be computed, as explained above with reference to equations (1). Of course, the phase fraction of a two phase fluid can be made using this system as well, in which case the mathematical system for determining the phase fractions is over constrained, meaning that there are more equations than variables to be solved. Such over constraining may improve the accuracy of the system or allow for double-checking of computed phase fraction values.

It is not strictly necessary to use a single phase fraction meter 3 in conjunction with the mandrel 4 as disclosed above. In this sense, it should be understood that because the preferred phase fraction meter 3 comprises a number of sensor wraps, those wraps appearing in zones 5 and 6 respectively could be viewed as constituting two separate phase fraction meters. In short, two separate phase fraction meters, whether or not multiplexed, may be used to respectively determine the speed of sound at the location of and adjacent to the mandrel 4.

Because the composition of the fluid flowing in the pipe 10 may change over time, it is preferable to simultaneously measure the speed of sound in the differing sections of compliancy, but this is not strictly necessary. For example, for fluids known to be relatively constant in composition over a certain time period, speed of sound measurements can be made before or after the mandrel 4 is deployed into position within the phase fraction meter 3. For example, the speed of sound ($a_{measured,1}$) may be measured without the mandrel 4 within the meter 3, or without a mandrel 4 deployed in the pipe 10 at all. Shortly thereafter, and assuming the composition of the fluid does not appreciably change, the mandrel 4 may be deployed within the meter, and in fact may completely fill up the meter, and a second speed of sound measurement taken ($a_{measured,2}$). As before, such a procedure allows the density of the fluid, $\rho_{mix}$, and the phase fractions to be calculated.

Figure 2:
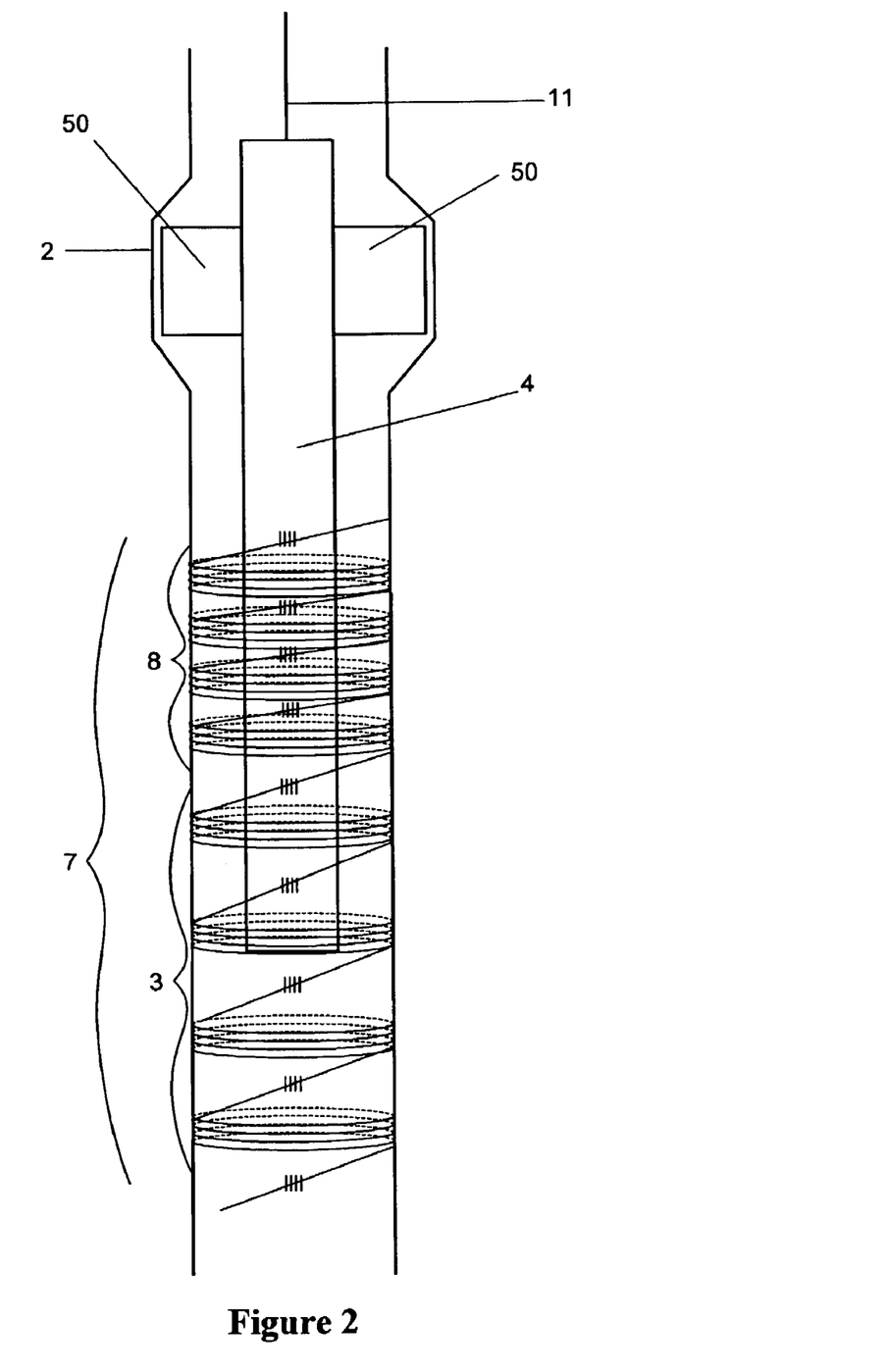
FIG. 2 is a diagram of an apparatus as in FIG. 1b, and further comprising a flow velocity meter.

U.S. patent application Ser. No. 09/740,760, entitled "Apparatus for Sensing Fluid in a Pipe," filed Nov. 29, 2000, and incorporated herein by reference in its entirety, describes an integrated flow meter apparatus 7, as shown in FIG. 2. Such an integrated apparatus 7 can comprise a phase fraction meter 3, as described above and a flow velocity meter 8. The flow velocity meter 8 can constitute the meter disclosed in U.S. patent application Ser. No. 09/346,607, entitled "Flow Rate Measurement Using Unsteady Pressures," filed Jul. 2, 1999, which is incorporated by reference herein in its entirety. The details of this flow velocity meter are not disclosed herein, but like the phase fraction meter preferably comprises passive fiber optic based sensors employing or working in conjunction with fiber Bragg gratings (FBGs) as shown. More specifically, the flow velocity meter 8 comprises a plurality of sensor wraps separated by FBGs, similar to the arrangement of the phase fraction meter 3 shown in FIG. 1b.

The function of sensing arrays 3 and 8, and the information gathered to perform that function, are distinct. As noted in the incorporated references, it is of interest to measure the speed at which sound propagates with respect to the fluid moving in the pipe. Therefore, although in most case the flow velocity is negligible compared to the sound speed, the effect of non-negligible flow rates can be accounted for in a straight forward manner, with the fluid velocity adding to the propagation velocity in the direction of the flow and subtracting from the propagation velocity against the flow.

The local vortical pressure variations that are sensed by the flow velocity meter 8 travel with the fluid flow, and therefore flow at approximately the same axial velocity as the fluid. These local pressure variations have small coherence lengths (sometimes referred to as scale lengths) typically on the order of one to ten (1–10) pipe diameters. The flow velocity sensors within the meter are spaced closely together to better detect these scales lengths. As one skilled in the art would recognize, the spacing between the sensors in the flow velocity meter 8 should be adjusted to maximize their sensitivity to the vortical variations in a given application. In contrast, the acoustic pressure variations that are sensed by the phase fraction meter 3 are pressure variations that travel at the speed of sound through the fluid. Thus, these acoustic pressure variations have coherence lengths on the order of one hundred to ten thousand (100–10,000) pipe diameters, orders of magnitude greater than that of the aforesaid vortical pressure variations. Therefore, as one skilled in the art would recognize, the spacing between the sensors in the phase fraction meter will be further apart than the velocity sensors, and similarly adjusted to maximize their sensitivity to the acoustic variations in a given application.

The performance of the flow velocity meter 8, as it is used in the prior art, typically suffers over the life of the well owing to gas breakthrough and decreasing production rates. However, performance is enhanced and this problem mitigated by use of the disclosed compliant mandrel 9, as shown in FIG. 2, because the mandrel partially blocks the flow in the region of the velocity meter 8 thereby increasing the flow velocity in the region. Such an integrated flow meter can provide information about the phase fraction and flow velocity of a three-phase mixture, with the added constriction bringing the flow velocity back up into measurable range. Additionally, the added cross sectional compliance enables a phase fraction determination of a three component (oil, gas, water) flow, as disclosed above with reference to FIG. 1b. It should be recognized that although FIG. 2 shows an embodiment having both a flow velocity meter 8 and a phase fraction meter 3, a flow velocity meter, in and of itself, would benefit from the constriction provided by the compliant mandrel, independent of the phase fraction meter.

U.S. patent application Ser. No. 10/186,382, entitled "Venturi Augmented Flow Meter," filed Jun. 28, 2002, and which is incorporated herein by reference, describes an integrated flow meter comprising a phase fraction meter 3 and/or a flow velocity meter 8 as described above, and further comprising a venturi 11 (see FIG. 3a). The venturi 11 adds several beneficial attributes to the integrated flow meter. For example, the venturi 11 serves as a homogenizer, causing the fluid to flow more uniformly and providing a well-mixed input for the flow velocity and/or the phase fraction meters. Also, the increased velocity of the fluid through the venturi 11 adds acoustic energy to the fluid, making it easier for the meters to detect the propagating acoustics in the fluid mixture.

Figure 3A:
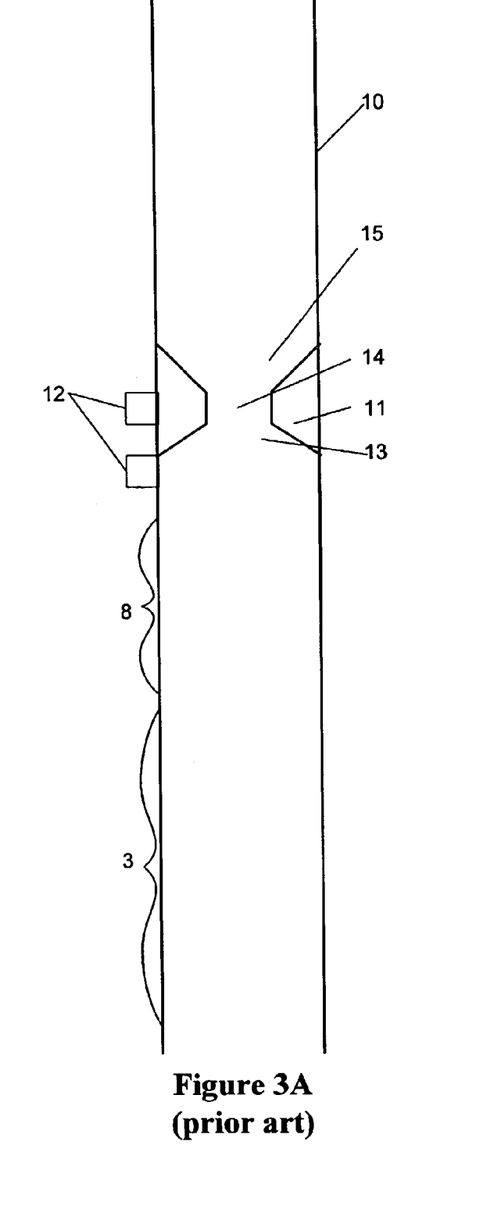
FIG. 3a is a diagram of a prior art flow meter comprising a phase fraction meter, a flow velocity meter, and a fixed venturi coupled to the inside of the production pipe.

Additionally, since the venturi measures the momentum of the fluid when used in conjunction with a velocity meter, the venturi can assist in determining the phase fractions in a three-phase mixture. The pressure differential across a venturi is proportional to the flow momentum of the fluid, i.e.:

$$\Delta P = c\rho_{mix}U^2_{mix} \qquad (6)$$

where $\Delta P$ is the pressure differential measured across the venturi as measured by pressure sensors 12, c is a fitting parameter, $\rho_{mix}$ is the density of the mixture, and $u_{mix}$ is the velocity of the mixture. In an integrated flow meter, the flow velocity meter measures $u_{mix}$ and pressure sensors across the venturi measure $\Delta P$, thus allowing the determination of $\rho_{mix}$. The density, in combination with the phase fraction measurements according to equation (1), allows for the determination of the phase fraction for a three component mixture using the system of equations described above.

Figure 3B:
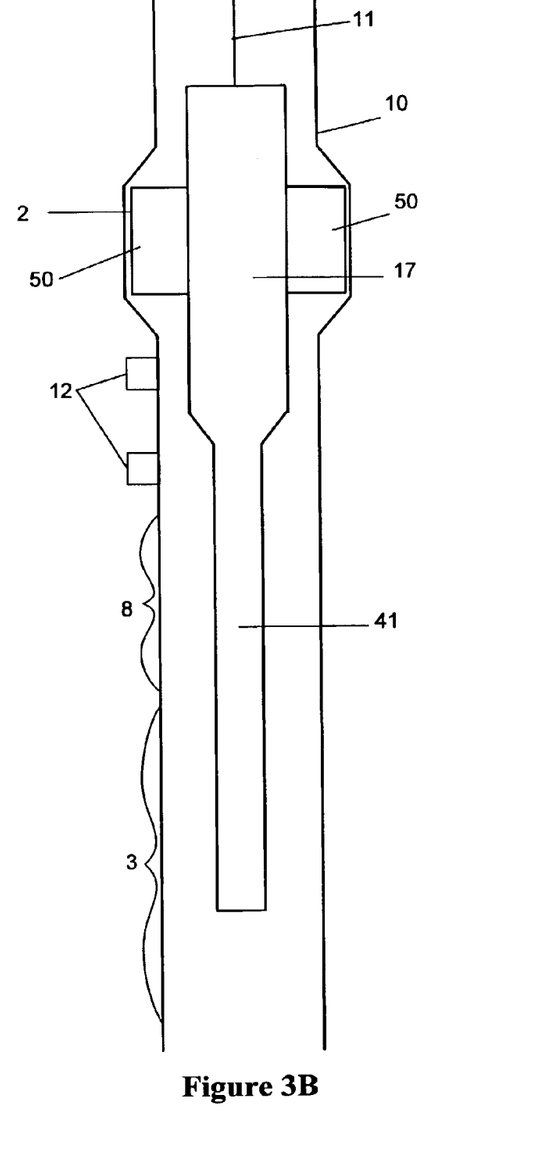
FIG. 3b is a diagram of an apparatus as in FIG. 3b, but wherein the fixed venturi is replaced by a deployable compliant mandrel constituting an annular venturi.

While FIG. 3a depicts a venturi 11 permanently affixed to the pipe 10 as disclosed in application Ser. No. 10/186,382, the deployable mandrel of the present invention can constitute an annular venturi 17 as depicted in FIG. 3b. The fluid flows around a constriction in an annular venturi 17, as opposed to through the constriction as in the affixed venturi 11, but otherwise it functions similarly in the system. Therefore, by measuring the pressure drop across the venturi 17 with pressure sensors 12 at annular locations 18, and by using the flow velocity measured by the flow velocity meter 8, the density of the fluid can be determined from equation (6). This provides enough known variables (including $\rho_{mix}$) to solve equations (1) for a three component fluid without the need to assess or compute cross sectional compliances as disclosed in equations (2), (5), and (4). Of course however, these compliancy-related equations can still be used to improve system accuracy, or to act as a double check on the computed phase fractions determined by equations (1). In other words, the compliancy of the portion 41 of the venturi 17 which appears within the phase fraction meter 3 can be computed vis-a-vis the pipe 10 per equation (5), which ultimately can be used to compute (or recompute) $\rho_{mix}$ per equation (4). In this sense, the venturi can be used to overconstrain the system by providing a means for computing $\rho_{mix}$ in two different ways. This excess of information allows for an internal calibration of the meters by comparing the density measurements determined by the two separate methods. As disclosed above, the portion 41 of the venturi 17 may be deployed partially into the measuring region of the phase fraction meter 3 to allow for a simultaneous density measurement, or a plurality of phase fraction meters may be utilized for a simultaneous measurement, or the portion 41 may be fully or partially deployed before or after an unobstructed measurement by the phase fraction meter 3.

As one skilled in the art will appreciate, especially in light of the incorporated references, the various optical signals from the sensors and flow meters disclosed herein are preferably sent to a computer to process and evaluate the received data and to make the necessary mathematical calculations disclosed herein. If the disclosed sensors and/or flow meters are fiber optic based, the signals will first be sent to an optoelectric detector(s) to transform the optical signals into electrical signals readable by a standard computer or signal processor, as is well known. Moreover, the optical devices may be multiplexed together, e.g., by wavelength-division multiplexing or time-division multiplexing, which would allow a single fiber to carry the signals from the sensors and/or flow meter(s) to the necessary electronics, as is well known. In an oil/gas application, the sensors and/or flow meter(s) will preferably be deployed down the oil well and connected by a fiber optic cable(s) to the detection electronics and computer(s) residing on the earth's surface and accessible by an operator.

In summary, a deployable mandrel according to the present invention improves downhole multiphase flow measurements in several ways. By providing an additional cross sectional compliance, the deployable mandrel allows the determination of the density of the fluid mixture via two speed of sound measurements and thereby provides sufficient information to solve for the phase fractions of a three phase fluid. Also, the mandrel provides a flow blockage, thereby facilitating a flow velocity measurement, even when the flow rate is so low that it would have previously been difficult to measure. The mandrel further provides a constriction, i.e., a venturi, allowing an independent determination of the fluid density and therefore a further means of solving for the phase fraction of a three-phase fluid.

A further benefit of the present invention is that the mandrel can be deployed in response to changing flow parameters and fluid compositions. Different sizes and compliances of mandrels can be chosen according to the specific conditions. The benefits disclosed herein can be realized independently of the orientation of the pipe, be it horizontal, vertical, or otherwise. As one skilled in the art would recognize, the order of each individual sensor and/or sensor array(s) along the flow path can be changed according to the specific desired configuration.

Furthermore, when the ability to deploy a compliant mandrel insert at a later data is contemplated prior to the initial deployment of a sound-speed-based, two phase flow meter, the compliant mandrel insert a can be design in conjunction with the initial two phase flow meter such that the compliant mandrel can be deployed to augment the flow measurement when and if it becomes necessary over the life of the well.

What is claimed is:

1. A system for measuring at least one parameter of a fluid flowing in a conduit, the conduit having a first cross sectional compliance, the system comprising:
    at least one first flow meter disposed on the outside of the conduit for measuring at least one parameter of the fluid mixture, wherein the flow meter has a length along the axis of the conduit;
    a mandrel disposed within the conduit and at least partially within the length of the flow meter, the mandrel configured to provide a second cross sectional compliance different than the first cross sectional compliance; and
    a line coupled to the mandrel for disposing the mandrel into position within the conduit.

2. The system of claim 1, wherein the flow meter comprises a velocity meter.

3. The system of claim 1, wherein the flow meter comprises a meter for determining the speed of sound of the fluid.

4. The system of claim 1, wherein the flow meter is fiber optic based.

5. The system of claim 4, wherein the flow meter comprises a series of wraps wrapped around the outside of the conduit.

6. The system of claim 5, further comprising fiber Bragg gratings between the wraps.

7. The system of claim 1, wherein the mandrel modulates the first cross sectional compliance of the conduit.

8. The system of claim 1, wherein the mandrel is hollow.

9. The system of claim 1, wherein the mandrel is evacuated.

10. The system of claim 1, wherein the conduit further comprises a seat for holding the mandrel.

11. The system of claim 1, wherein the mandrel comprises an annular venturi having first diameter and a second diameter smaller than the first diameter.

12. The system of claim 11, further comprising a first pressure sensor for measuring the pressure of the fluid proximate to the first diameter and a second pressure sensor for measuring the pressure of the fluid proximate to the second diameter.

13. The system of claim 1, further comprising a second flow meter, wherein the mandrel is not disposed within the second flow meter.

14. The system of claim 1, wherein the conduit comprises a production pipe for a well.

15. A method for determining the phase fractions of a fluid mixture flowing within a conduit, wherein the conduit comprises at least one first flow meter disposed on the outside of the conduit along a first axial length of the conduit, the method comprising:
    disposing a mandrel within the conduit at least partially within the first length of the first flow meter to change a cross sectional compliance, wherein disposing the mandrel comprises seating the mandrel within the conduit;
    computing the density of the fluid mixture using data from at least the first flow meter; and
    computing the phase fractions of the components in the fluid mixture using the computed density of the mixture.

16. The method of claim 15, wherein disposing the mandrel comprises the use of a line.

17. The method of claim 15, wherein the flow meter comprises a meter for measuring the speed of sound of the fluid, and wherein the density of the fluid is computed using the measured speed of sound.

18. The method of claim 15, wherein the flow meter is fiber optic based.

19. The method of claim 18, wherein the flow meter comprises a series of wraps wrapped around the outside of the conduit.

20. The method of claim 19, further comprising fiber Bragg gratings between the wraps.

21. The method of claim 15, wherein the mandrel is hollow.

22. The method of claim 15, wherein the mandrel is evacuated.

23. The method of claim 15, wherein computing the density comprises
    measuring a first speed of sound of the fluid mixture where the mandrel is disposed within the first length; and
    measuring a second speed of sound of the fluid mixture where the mandrel is not disposed within the first length.

24. The method of claim 15, wherein at least one second flow meter is disposed on the outside of the conduit at a location separate from the first axial length, and wherein the mandrel is not disposed within the conduit proximate to the second flow meter, and wherein computing the density comprises
    measuring a first speed of sound of the fluid mixture using the first flow meter; and
    measuring a second speed of sound of the fluid mixture using the second flow meter.

25. The method of claim 15, wherein the mandrel comprises an annular venturi having first diameter and a second diameter smaller than the first diameter.

26. The method of claim 25, further comprising measuring the pressure of the fluid mixture proximate to the first diameter and the second diameter.

27. The method of claim 15, wherein the conduit comprises a production pipe for a well.

28. A method for determining the phase fractions of a fluid mixture flowing within a conduit, comprising in no particular order:

disposing a mandrel within me conduit at a first location to change a cross sectional compliance, wherein disposing the mandrel comprises seating the mandrel within the conduit;

measuring a first speed of sound of the fluid at the first location;

measuring a second speed of sound of the fluid at a second location different from the first location; and using the first speed of sound and the second speed of sound to calculate the phase fraction of the fluid mixture.

29. The method of claim 28, wherein the cross sectional compliancies at the first and second locations are different.

30. The method of claim 28, wherein disposing the mandrel comprises the use of a line.

31. The method of claim 28, wherein the first speed of sound and second speed of sound are measured using at least one flow meter disposed on the outside of the conduit.

32. The method of claim 31, wherein the flow meter is fiber optic based.

33. The method of claim 32, wherein the flow meter comprises a series of wraps wrapped around the outside of the conduit.

34. The method of claim 33, further comprising fiber Bragg gratings between the wraps.

35. The method of claim 28, wherein the mandrel is hollow.

36. The method of claim 28, wherein the mandrel is evacuated.

37. The method of claim 28, wherein the mandrel comprises an annular venturi.

38. The method of claim 28, wherein using the first and second speed of sounds comprises computing the density of the fluid mixture.

39. The method of claim 28, wherein the first speed of sound is measured using a first flow meter and the second speed of sound is measured using a second flow meter.

40. The method of claim 28, wherein the first and second speed of sound are measured using a single flow meter.

41. The method of claim 28, wherein the conduit comprises a production pipe for a well.

42. A method for determining the density of a fluid mixture flowing within a conduit, comprising in no particular order:

disposing a mandrel within the conduit at a first location to change a cross sectional compliance, wherein disposing the mandrel comprises the use of a line;

measuring a first speed of sound of the fluid at the first location;

measuring a second speed of sound of the fluid at a second location different from the first location; and using the first speed of sound and the second speed of sound to calculate the density of the fluid mixture.

43. The method of claim 42, wherein the cross sectional compliancies at the first and second locations are different.

44. The method of claim 42, wherein disposing the mandrel comprises seating the mandrel within the conduit.

45. The method of claim 42, wherein the first speed of sound and second speed of sound are measured using at least one flow meter disposed on the outside of the conduit.

46. The method of claim 45, wherein the flow meter is fiber optic based.

47. The method of claim 46, wherein the flow meter comprises a series of wraps wrapped around the outside of the conduit.

48. The method of claim 47, further comprising fiber Bragg gratings between the wraps.

49. The method of claim 42, wherein the mandrel is hollow.

50. The method of claim 42, wherein the mandrel is evacuated.

51. The method of claim 42, wherein the mandrel comprises a venturi.

52. The method of claim 42, wherein the first speed of sound is measured using a first flow meter and the second speed of sound is measured using a second flow meter.

53. The method of claim 42, wherein the first and second speed of sound are measured using a single flow meter.

54. The method of claim 42, wherein the conduit comprises a production pipe for a well.

* * * * *